United States Patent [19]

Huthmacher et al.

[11] Patent Number: 5,091,554
[45] Date of Patent: Feb. 25, 1992

[54] METHOD OF PREPARING 1,3,3-TRIMETHYL-5-OXO-CYCLOHEXANE CARBONITRILE

[75] Inventors: Klaus Huthmacher, Gelnhausen; Hermann Schmitt, Rodenbach, both of Fed. Rep. of Germany

[73] Assignee: Degussa AG, Fed. Rep. of Germany

[21] Appl. No.: 622,786

[22] Filed: Dec. 5, 1990

[30] Foreign Application Priority Data

Dec. 21, 1989 [DE] Fed. Rep. of Germany ....... 3942371

[51] Int. Cl.$^5$ .......................................... C07C 253/10
[52] U.S. Cl. .................................................... 558/341
[58] Field of Search ........................................ 558/341

[56] References Cited

U.S. PATENT DOCUMENTS

| | | | |
|---|---|---|---|
| 4,299,775 | 11/1981 | Dubreux | 558/341 |
| 5,011,968 | 4/1991 | Thunberg et al. | 558/341 |

FOREIGN PATENT DOCUMENTS

| | | | |
|---|---|---|---|
| 1240854 | 10/1964 | Fed. Rep. of Germany | 558/341 |
| 0116038 | 7/1982 | Japan | 558/341 |

Primary Examiner—Joseph Paul Brust
Attorney, Agent, or Firm—Cushman, Darby & Cushman

[57] ABSTRACT

Hydrogen cyanide is added to isophorone for the preparation of 1,3,3-trimethyl-5-oxo-carbonitrile in the presence of lithium hydroxide in an amount in a range of 0.005 to 5 mole % at 100° to 160° C. The yield is higher and the space-time yield is better than was possible when using other alkaline acting alkali compounds.

4 Claims, No Drawings

METHOD OF PREPARING 1,3,3-TRIMETHYL-5-OXO-CYCLOHEXANE CARBONITRILE

The present invention relates to a method of preparing 1,3,3-trimethyl-5-oxo-cyclohexane carbonitrile by means of the addition of hydrogen cyanide to isophorone in the presence of an alkaline compound as catalyst at 100° to 160° C. The method of the invention may be used for preparing 1,3,3-trimethyl-5-oxo-cyclohexane carbonitrile, which is also designated as 3-cyano-3,5,5-trimethylcyclohexanone or simply isophorone nitrile, with highly efficient use of the catalyst.

BACKGROUND OF THE INVENTION

The addition of hydrogen cyanide to isophorone has long been know. The reaction takes place in a base-catalyzed manner at an elevated temperature.

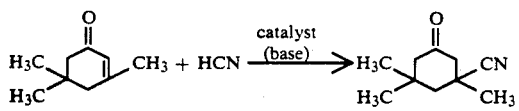

Published German patent application DE-AS 10 85 871 discloses a method in which isophorone and hydrogen cyanide are reacted at 125° to 275° C. in the presence of a strongly alkaline catalyst which forms cyanide ions and preferably in the presence of a strong polar solvent such as dimethylformamide or dimethylacetamide. The hydrocyanic acid is added essentially at the speed with which it is reacted. Among the catalysts mentioned are alkali metals and their carbonates, alkali- and alkaline-earth alcoholates, -oxides, -hydroxides and -cyanides, as well as amines and quaternary ammonium bases are named as catalysts. The catalytic concentration is given at 0.1 to 20% by weight relative to the weight of the reaction mixture. After the reaction, the reaction mixture is combined with phosphoric acid in order to neutralize the catalyst and it is subsequently distilled. As is apparent from the relevant example of this patent, the hydrogen cyanide had to be introduced very slowly, which resulted in an unsatisfactory space-time yield. A further disadvantage is the fact that a heterogeneous solvent had to be used, which increased the expense for the workup of the reaction mixture. Isophorone nitrile was obtained in only an average yield and moderate purity.

German patent DE-PS 12 40 854 discloses an improvement of the above-mentioned method in that a higher yield can be achieved in the absence of a solvent with lesser amounts of catalyst, to wit, $10^{-1}$ to $10^{-3}\%$ by weight relative to the reaction mixture. However, this improvement did not shorten the reaction time - 4 hours dwell time in the main reactor and 1 hour in each of two post-reactors in accordance with Example 2 of the patent.

The applicant of published Japanese application JP-A 57-116038 attempted to improve the method cited referring to the previously evaluated DE-AS 10 85 871 and DE-PS 12 40 854. According to the comparison tests disclosed in the Japanese document, a yield of 53.7% was obtained using a methanolic NaOH solution as catalyst (0.9 ml 15% NaOH per 204 g isophorone) after a total reaction time of 4.5 hours and a yield of 71.1% was obtained using $K_2CO_3$ as catalyst (4.9 g $K_2CO_3$ per 192.2 g isophorone) and also using dimethylformamide.

In contrast published Japanese application JP-A-116038 teaches the reaction of hydrogen cyanide in the presence of basic catalysts such as e.g. alkali-metal cyanides, -carbonates, -oxides, -hydroxides and -alcoholates, and glycols with isophorone. The glycols are added in an amount 1 to 50 times greater than the catalyst. High yields of isophorone nitrile are disclosed in the examples, but the reaction times using sodium and potassium carbonate or sodium cyanide are in the range of the methods already previously known at the time. The space-time yield thus continued to remain unsatisfactory. As a result of the use of glycols, the workup becomes more expensive and the economy is reduced.

Other methods which have been disclosed involve the use of quaternary ammonium or phosphonium hydroxides - cf. published Japanese application JP-A 61-33157 - or diazabicycloalkenes - cf. published Japanese application JPA 61-33158 - as catalyst. However, these catalysts are quite expensive.

German patent DE-PS 12 40 521 describes a method in which the reaction between isophorone and hydrogen cyanide takes place in the presence of alkaline catalysts placed on solid carriers at 50° to 350 C. Preferably, alkali hydroxides or alkali cyanides are deposited on the carriers as catalysts. The preparation of the carrier catalysts is quite complicated and carrying-out the reaction is expensive, since the HCN concentration in the reaction mixture must be maintained low. For this purpose, the hydrocyanic acid has to be diluted in the gas phase with nitrogen. The method thus does not appear to be economical for industrial application in spite of the high yields indicated.

Finally, 1,3,3-trimethyl-5-oxo-cyclohexane carbonitrile can also be obtained from isophorone and alkali cyanides in an aqueous-organic two-phase system in the presence of a phase-transfer catalyst - see published European application EP B 028 179. However, this method requires the use of an alkali cyanide, which is more expensive than hydrogen cyanide as well as a not inconsiderable amount of an expensive transfer catalyst; the workup of the aqueous phase results in a considerable accumulation of salt and consequently problems of disposal.

SUMMARY OF THE INVENTION

The object of the present invention is to improve the method of preparing 1,3,3-trimethyl-5-oxo-cyclohexane carbonitrile by the addition of hydrogen cyanide to isophorone in the presence of an alkaline acting alkali compound as catalyst at 100° to 160° C. in such a manner that a higher space-time yield results with a yield of approximately 90% and more. A further object of the invention is to provide such a method which is simple to carry out and which is not dependent on the use of expensive catalysts and/or auxiliary substances and/or heterogeneous solvents.

These and other objects are achieved by using lithium hydroxide as catalyst and carrying out the reaction in the presence of 0.005 to 5 mol % catalyst relative to isophorone.

In accordance with the invention it has been determined that the catalytic effectiveness of lithium hydroxide exceeds that of the other alkali hydroxides to a surprising extent. Although alkaline acting alkali compounds were generally known in the art and although hydroxides, cyanides and carbonates of sodium and potassium were used as catalysts in the examples of the cited patents and patent applications, it could not have been foreseen that lithium hydroxide would be able to provide an extraordinarily high catalytic activity.

The surprising effect of lithium hydroxide had not bee recognized previously. This effect is shown below in the comparison of the examples in accordance with the invention with the reference examples 1 and 2 using sodium- and potassium hydroxide as catalyst; NaOH and KOH exhibit only a moderate activity if they are used without additional auxiliary substances and economic product yields can not be obtained with them. By contrast, yields near, and usually above, 90% are achieved with lithium hydroxide - that is, the polymerization of hydrocyanic acid and the oligomerization of isophorone, known as side reactions, are essentially completely suppressed.

The extremely short reaction times achievable with LiOH are excellent—under comparable conditions 5 to 15 minutes according to the invention compared with 3 to 4 hours and longer according to the state of the art. On the whole, the method of the invention can be carried out with high spacetime yields.

Solvents or other auxiliary substances are generally not necessary in the method of the invention; however, an excess of isophorone in relation to hydrogen cyanide is generally used; a molar ratio of isophorone to hydrogen cyanide in a range of 1:1 to 1 to 5 to 1, especially 1.5 to 1 to 2.5 to 1, is preferred.

It could not have been foreseen that the catalytic activity of lithium hydroxide is also considerably greater than that of other alkaline acting lithium compounds such as lithium cyanide. Lithium cyanide is also cited e.g. as catalyst in published German patent application DE-AS 10 85 871; however, a yield of only 51.5% was obtained with this catalyst, as is apparent from reference Example 3.

The catalytic amount of LiOH used in accordance with the invention is 0.005 to 5 mole %, preferably 0.1 to 2 mole % relative to isophorone. The catalytic amount must at least suffice, if liquid hydrogen cyanide stabilized with mineral acid is used, to convert the mineral acid into a salt and, additionally, to maintain a catalytically active amount of LiOH in the reaction mixture. If hydrogen cyanide which is free of mineral acid is used, the catalytic amount can generally be limited to less than 1 mole %.

The addition of HCN to isophorone catalyzed with LiOH is generally carried out at 100° to 160° C., preferably between 120° and 160° C. The addition takes place exothermally so that the effective rate of addition of hydrogen cyanide is essentially a function only of the conditions of the apparatus, especially of the condenser capacity. A postreaction time is not necessary. The reaction mixture can be transferred for workup substantially immediately after the rapid mixing of the reactants. According to an especially preferred embodiment, the isophorone-catalyst mixture, heated to approximately 130° C., is combined with hydrogen cyanide while maintaining a temperature in a range between 135° and 150° C.; the reaction mixture obtained in this manne is transferred for workup without a postreaction time. The workup usually includes neutralizing the catalyst or separating it from the reaction mixture as well as separating the 1,3,3-trimethyl-5-oxo-cyclohexane carbonitrile from the excess isophorone and from small amounts of impurities by distillation. The reaction mixture can be treated e.g. with a little water in order to wash out the lithium compounds; alternatively, LiOH can be neutralized before the fractional distillation with a strong acid such as e.g. phosphoric acid or p-toluenesulfonic acid.

DETAILED DESCRIPTION OF PREFERRED EMBODIMENTS

The invention is illustrated in the following examples and reference examples.

EXAMPLE 1

345 g (367 ml; 2.5 moles) isophorone and 0.8 g (0.033 mole) lithium hydroxide are placed in a reaction apparatus with agitator, condenser, thermometer and dropping funnel. A total of 40.5 g (59 ml; 1.5 moles) liquid hydrogen cyanide are added to the mixture at 135° C. within 10 minutes. The reaction temperature rises to approximately 145° C. This temperature is maintained by cooling. Then, 6.8 g (0.036 mole) p-toluenesulfonic acid are added. For the workup, the excess isophorone is distilled off via a distillation column under a water-jet vacuum and the residue is purified in a high vacuum; the following are obtained:

134.0 g: isophorone (boiling point$_{15}$: 89°-110° C.)

220.5 g: isophorone nitrile (boiling point$_{0.1}$: 105°-110° C.); corresponding to 89.1% of theory relative to hydrogen cyanide added

EXAMPLE 2

345 g (376 ml; 2.5 moles) isophorone and 0.8 g (0.033 mole) lithium hydroxide are placed in a reaction apparatus as described in Example 1. From a total of 27 g (approximately 39 ml; 1 mole) liquid hydrogen cyanide, approximately 10 ml are added to the receiver and the mixture is heated to 135° C. The remaining hydrogen cyanide is added drop-by-drop via the dropping funnel within 5 minutes and the rising reaction temperature maintained at 140° C. by cooling. Thereafter, 8 g toluenesulfonic acid are added and excess isophorone distilled off from the reaction mixture via a column in a vacuum. The residue is then purified in a high vacuum; the following are obtained:

187.1 g: isophorone (boiling point$_{15}$: 88°-90° C.)

155.5 g: isohporone nitrile (boiling point$_{0.1}$: 105°-110° C.), corresponding to 94.2% of theory relative to hydrogen cyanide added

EXAMPLE 3

276 g (approximately 300 ml; 2 moles) isophorone and 0.8 g (0.033 mole) lithium hydroxide are placed in an agitating apparatus as in Example 1 and heated to 150° C. Then, 27 g (39 ml; 1 mole) liquid hydrogen cyanide are added drop-by-drop within 10 min.; the reaction temperature rises to 168° C. Then, 2.2 ml 85% phosphoric acid are added and the excess isophorone distilled off from the reaction mixture via a column under vacuum; the residue is purified in a high vacuum; the following are obtained:

134.6 g: isophorone 155.7 g: isophorone nitrile (boiling point$_2$: 115°-122° C.), corresponding to 94.3% of theory relative to hydrogen cyanide added

EXAMPLE 4

186 kg (1347.8 moles) isophorone and 0.452 kg (18.8 moles) lithium hydroxide are placed in an agitated tank apparatus and heated to 135° C. Then, 22.8 kg (844.4 moles) hydrogen cyanide are introduced with cooling in such a manner that the reaction temperature does not exceed 145° C. Then, 3.84 kg p-toluenesulfonic acid are added and the excess isophorone distilled off under vacuum via a column. The bottom is purified in a high vacuum. The following are obtained:

68.5 kg: isophorone (boiling point$_{30}$: 118°-120° C.)

134.0 kg: isophorone nitrile (boiling point$_2$: 115°-120° C.), corresponding to 96.1% of theory relative to hydrogen cyanide added

EXAMPLE 5

Example 1 was repeated adding 0.3 g (= 012 mole) lithium hydroxide instead of 0.8 g (= 0.033 mole) lithium hydroxide. The yield of isophorone nitrile was 93.3% relative to hydrogen cyanide added. No hydrogen cyanide stabilized with acid was used.

(Liquid hydrogen cyanide which had been stabilized with approximately 1% by weight phosphoric acid was used in Examples 1 to 4 and in reference Examples 1 to 3.)

REFERENCE EXAMPLE 1

345 g (376 ml; 2.5 moles) isophorone and 2.2 g (0.033 mole) potassium hydroxide (85%) were placed in a reaction apparatus with agitator, condenser, thermometer and dropping funnel. From a total of 40.5 g (59 ml; 1.5 moles) hydrogen cyanide, 9 ml are added to the receiver and the mixture is heated to 135° C. The remaining hydrogen cyanide is allowed to run in via the dropping funnel within 3 hours; the temperature drops to approximately 110° C. thereby and hydrogen cyanide boils under a vigorous reflux. After the end of the addition, the mixture is agitated for 1.5 hours longer, during which time the temperature rises again to approximately 128° C. Then, 8 g p-toluenesulfonic acid are added and the excess isophorone distilled off in a water-jet vacuum via a column. The residue is purified in a high vacuum; the following are obtained:

213 g: isophorone (boiling point$_{15}$: 89°-95° C.)

118 g: isohporone nitrile (boiling point$_{0.1}$: 100°-110° C.), corresponding to 47.6% of theory relative to hydrogen cyanide added

REFERENCE EXAMPLE 2

Amounts and execution were as in Reference Example 1; however, 1.3 g (0.033 mole) sodium hydroxide is used for catalysis. The following are obtained:

217.6 g: isophorone (boiling point$_{15}$: 89°-95° C.)

107.3 g: isophorone nitrile (boiling point$_{0.1}$: 100°-107° C.), corresponding to 43.3% of theory relative to hydrogen cyanide added 45 g: residue

REFERENCE EXAMPLE 3

The reaction was carried out according to Example 1, using the equivalent amount of lithium cyanide (33 mmoles) instead of LiOH. 45 min. were required for the addition of hydrogen cyanide. After a postreaction of 30 min. at 145° C., the mixture was worked up and isophorone nitrile obtained in a yield of 51.5%.

What is claimed is:

1. In a method of preparing 1,3,3-trimethyl-5-oxo-cyclohexane carbonitrile by means of the addition of hydrogen cyanide to isophorone in the presence of an alkaline-acting alkali compound as catalyst at 100° to 160° C.;

the improvement in which the catalyst is lithium hydroxide and the reaction is carried out in the presence of 0.005 to 5 mole % catalyst relative to isophorone, the isophorone and hydrogen cyanide being reacted in a molar ratio in the range of 1.1 to 1 to 5 to 1 and no further solvent being used.

2. A method as set forth in claim 1 in which isophorone and hydrogen cyanide are reacted in a molar ratio of 1.5 to 1 to 2.5 to 1.

3. A method as set forth in any one of claims 1 and 3 in which liquid hydrogen cyanide is combined with isophorone containing the catalyst while maintaining a reaction temperature of 135°-150° C. and that the reaction mixture is transferred without postreaction delay to a workup, which comprises a neutralization or separation of the catalyst and distillation.

4. A method as set forth in any one of claims 1 and 3 in which the reaction is carried out in the presence of 0.1 to 2 mole % lithium hydroxide.

* * * * *